(12) United States Patent
Haack et al.

(10) Patent No.: US 8,231,574 B2
(45) Date of Patent: Jul. 31, 2012

(54) MANUAL IRRIGATION PUMP FOR INTRAPROCEDURAL IRRIGATION

(75) Inventors: Scott Haack, Chardon, OH (US); Aaron Boyce, Eastlake, OH (US); Chris Kaye, Concord, OH (US); Dean Secrest, Concord, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 0 days.

(21) Appl. No.: 12/781,487

(22) Filed: May 17, 2010

(65) Prior Publication Data

US 2010/0292644 A1    Nov. 18, 2010

Related U.S. Application Data

(60) Provisional application No. 61/178,754, filed on May 15, 2009.

(51) Int. Cl.
A61M 37/00 (2006.01)
(52) U.S. Cl. ......................................................... 604/132
(58) Field of Classification Search .................... 604/132
See application file for complete search history.

(56) References Cited

U.S. PATENT DOCUMENTS

| | | |
|---|---|---|
| 5,133,336 A | 7/1992 | Savitt et al. |
| 5,176,629 A | 1/1993 | Kullas et al. |
| 5,271,379 A | 12/1993 | Phan et al. |
| 5,505,707 A * | 4/1996 | Manzie et al. ................. 604/131 |
| 2005/0025646 A1 | 2/2005 | Miller et al. |
| 2007/0043262 A1 | 2/2007 | Levy et al. |
| 2007/0118078 A1* | 5/2007 | McNally et al. .............. 604/131 |
| 2007/0213668 A1 | 9/2007 | Spitz |
| 2008/0072970 A1 | 3/2008 | Gasser et al. |
| 2008/0132763 A1 | 6/2008 | Isaacson |
| 2008/0243054 A1 | 10/2008 | Mollstam et al. |

FOREIGN PATENT DOCUMENTS

| | | |
|---|---|---|
| WO | 2004/023987 A1 | 3/2004 |
| WO | 2005/011776 A1 | 2/2005 |

OTHER PUBLICATIONS

International Search Report and Written Opinion for corresponding International Application No. PCT/US2010/035125 dated Dec. 14, 2010.
International Preliminary Report on Patentability for corresponding International Application No. PCT/US2010/035125 dated Jun. 6, 2011.

* cited by examiner

*Primary Examiner* — Nicholas Lucchesi
*Assistant Examiner* — Jason Flick
(74) *Attorney, Agent, or Firm* — Renner, Otto, Boisselle & Sklar, LLP

(57) ABSTRACT

A disposable manual irrigation pump system comprises a manual foot pump operatively coupled to a fluid reservoir and an associated intraprocedural device. The pump system is configured to provide a substantially continuous fluid supply at a desired flow rate from the fluid reservoir to the associated intraprocedural device along a first direction without backflow of fluid along a direction opposite the first direction.

14 Claims, 10 Drawing Sheets

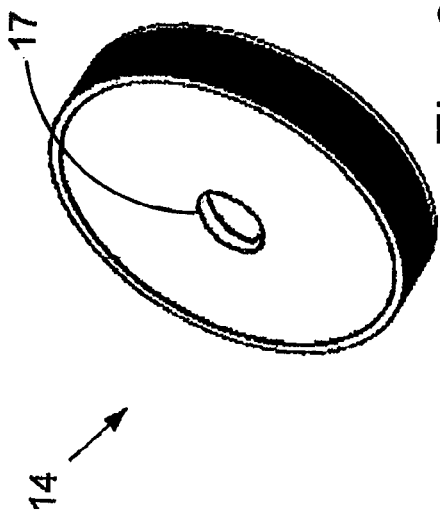
Fig. 3C
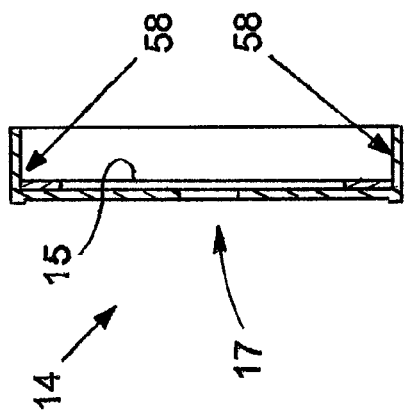
Fig. 3D
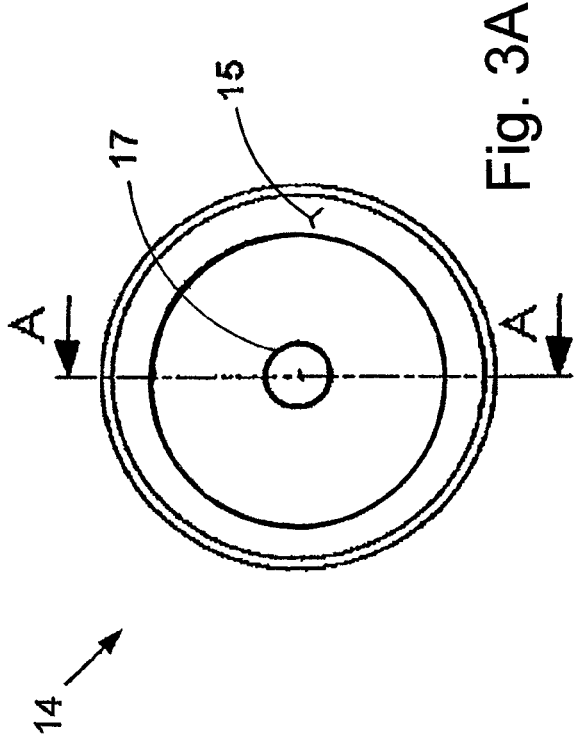
Fig. 3A
Fig. 3B

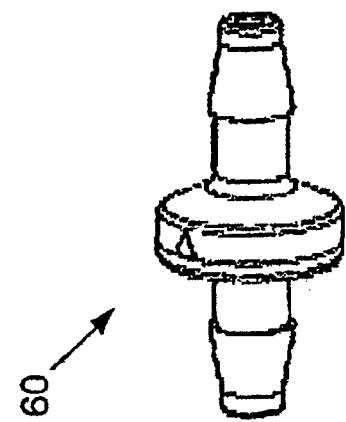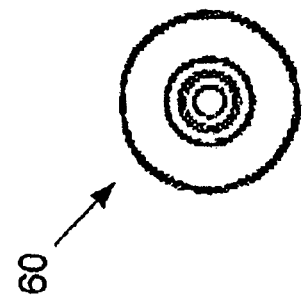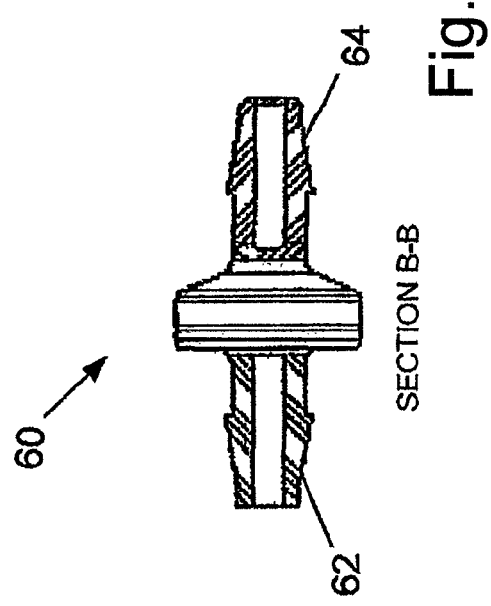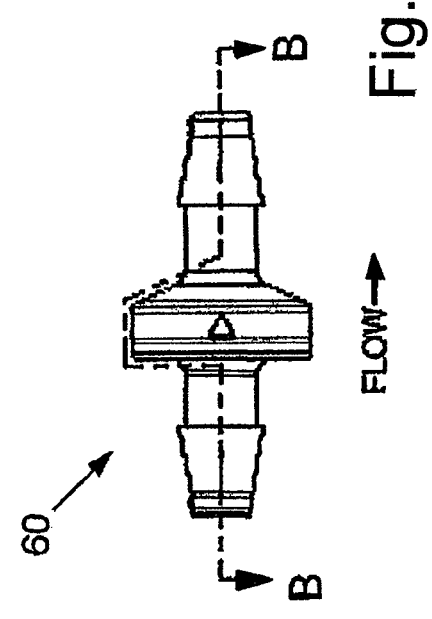
Fig. 6C
Fig. 6D
Fig. 6A
Fig. 6B

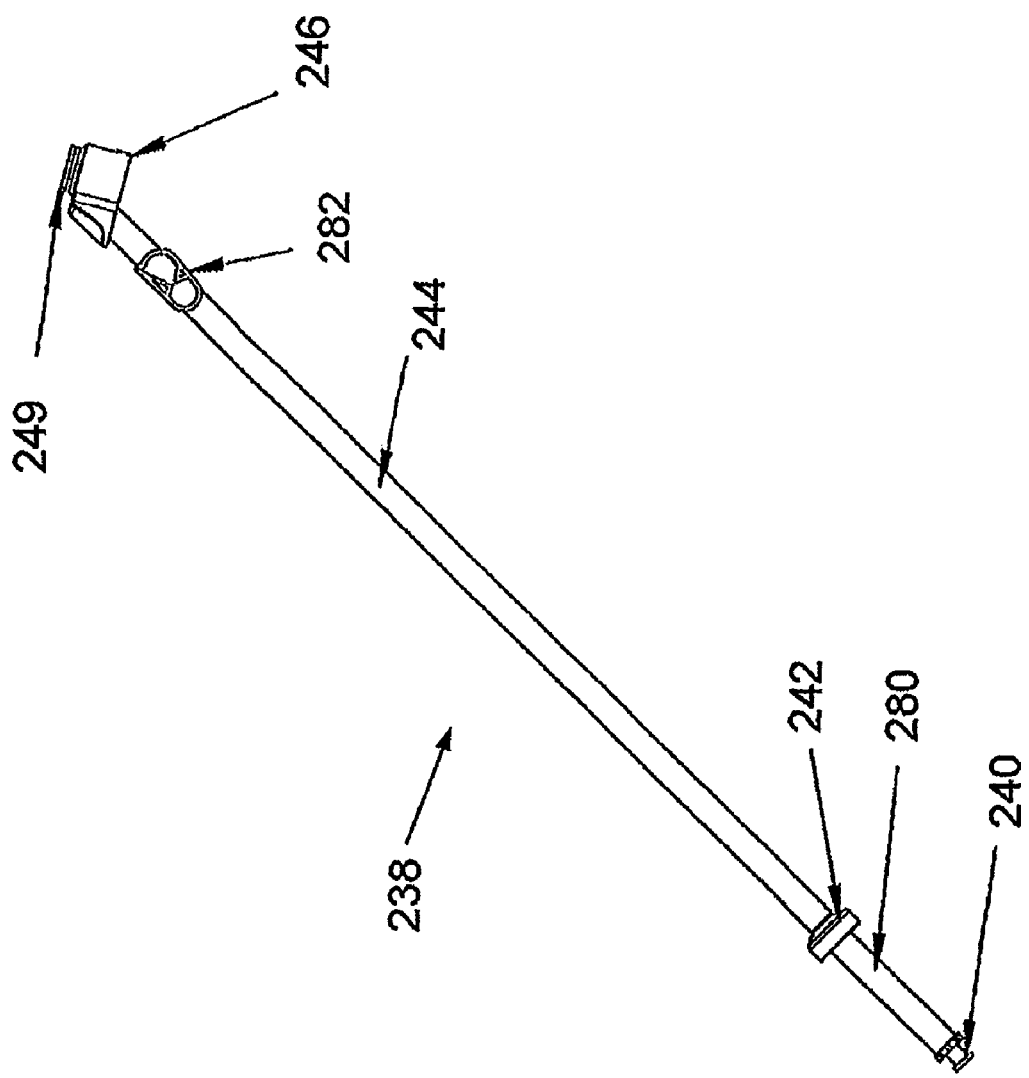

MANUAL IRRIGATION PUMP FOR INTRAPROCEDURAL IRRIGATION

The present invention relates generally to medical irrigation, and more particularly to a manual irrigation pump for intraprocedural irrigation.

BACKGROUND

During medical procedures when medical devices, such as an endoscope, are being used, oftentimes the physician performing the procedure requires irrigation fluid to clean off a procedural area. Moreover, often the irrigation channel of the endoscope cannot provide the required fluid.

To remedy this, the physician can use 60 cc syringes connected to an accessory water channel of the endoscope. The physician can instruct an assistant to actuate the syringe thereby increasing the flow of the fluid. After the fluid in the syringe has been discharged, the assistant retrieves another syringe and repeats the process. In some instances, an electrical or computer controlled pump may be used to eliminate some of the pitfalls of the 60 cc syringes by providing a continuous but low flow stream of fluid.

SUMMARY OF INVENTION

Intraprocedural irrigation systems are used to provide more irrigation fluid to an intraprocedural device to clean off a procedure site during the procedure. Some intraprocedural irrigation systems suffer from not being able to provide a continual, high flow rate stream of irrigation fluid to the procedure site thereby limiting a physician's view during endoscopic procedures. This is sometimes done so that the physician can better inspect or view (via an endoscope) patient's tissue. These devices are cost prohibitive, and prevent the physician from devoting all of her attention to the patient.

A system, apparatus, and method provide a means for manually delivering a fluid to an intraprocedural device, such as an endoscope, at a continual high flow rate. More particularly, the system, apparatus, and method draws fluid from a reservoir and delivers the fluid into the endoscope through a series of liquid supply tubes. The intraprocedural irrigation system is targeted for situations requiring copious amounts of fluid such as poor preparations in the colon, gastrointestinal bleeds, undigested food in the stomach, bezoars, blood clot removal, etc.

Aspects of the disclosed technology relate to a system, apparatus, and method for a disposable manual irrigation pump system. A manual foot pump is operatively coupled to a fluid reservoir and an associated intraprocedural device. The pump system is configured to provide a substantially continuous fluid supply at a desired flow rate from the fluid reservoir to the associated intraprocedural device along a first direction, without backflow of fluid along a direction opposite the first direction.

According to another embodiment, the disposable manual irrigation pump system may include a first liquid supply tube disposed between the pump and the reservoir and a second liquid supply tube disposed between the pump and the intraprocedural device.

According to another embodiment, the system further includes a connector configured to couple an end of the first liquid supply tube and an end of the second liquid supply tube to the pump.

According to another embodiment, the system further includes a first one-way valve disposed between the pump and the reservoir, wherein the first one-way valve allows fluid to flow from the reservoir to the pump without backflow of fluid from the pump to the reservoir.

According to another embodiment, the system further includes a second one-way valve disposed between the pump and the intraprocedural device, wherein the second one-way valve allows fluid to flow from the pump to the intraprocedural device without backflow of fluid from the intraprocedural device to the pump.

According to another embodiment, the system further includes a cap having threads suitable for coupling to a fluid reservoir having a first diameter and a stopper or second cap having threads suitable for coupling to a fluid reservoir having a second diameter.

According to another embodiment, the cap further includes an air vent configured to allow air to flow into the fluid reservoir.

According to another embodiment, the system further includes a liquid supply tube disposed in an opening of the cap.

According to another embodiment, the system further includes an irrigation valve configured to couple the intraprocedural device and the second liquid supply tube.

According to another embodiment, the system further includes a connector disposed between the pump and the reservoir, wherein the connector is configured to insure the fluid flow is unimpeded through first liquid supply tube.

According to another embodiment, the system further includes a third liquid supply tube disposed between the second liquid supply tube and the irrigation valve, wherein the third liquid supply tube is configured to couple the second liquid supply tube and the irrigation valve.

One aspect of the invention relates to a disposable irrigation pump system configured to deliver irrigation fluid to an intraprocedural device, the system includes: a fluid reservoir containing an irrigation fluid; an elastically deformable pump operably connected to the fluid reservoir and the intraprocedural device and containing irrigation fluid within, wherein the elastically deformable pump is configured to propel fluid into the intraprocedural device upon deformation of the pump by an operator; and a one way valve positioned between the pump and the intraprocedural device, the one way valve operably configured to provide passage of fluid from the pump to the intraprocedural device in response to operator deformation of the elastically deformable pump, and further configured to prevent fluid movement from the intraprocedural device to the pump upon release of the elastically deformable pump by the operator.

According to another embodiment, the elastically deformable pump includes at least one hollow for the reception of fluid therein.

According to another embodiment, the elastically deformable pump is further configured to return to an un-deformed state upon release by the operator.

Another aspect of the invention relates to a disposable irrigation pump system configured to deliver irrigation fluid to an intraprocedural device, the system includes: a fluid reservoir containing an irrigation fluid; a one way valve positioned between the fluid reservoir and the intraprocedural device, the one way valve and operably configured to provide passage of fluid from the fluid reservoir to the intraprocedural device and further configured to prevent to fluid passage from the intraprocedural device towards the fluid reservoir; and a pump operably configured to provide a controlled flow rate of fluid to the intraprocedural device in direct response to a force applied onto the pump by an operator, wherein the flow rate from the disposable irrigation pump system is directly proportional to the force applied by the operator.

According to another embodiment, a first rate of flow from the pump is a direct response to a first force applied to the pump by the operator.

According to another embodiment, when a second force is applied to the pump and the second force is greater than the first force, the rate of flow from the pump is greater than the first rate of flow.

According to another embodiment, when a third force is applied to the pump and the third force is less than the first force, the rate of flow from the pump is less than the first rate of flow.

According to another embodiment, the pump comprises a resilient material and when force is removed from a deformed pump, the pump returns to an un-deformed shape and the one way valve prevents fluid from being drawn into the pump from the portion of the disposable irrigation pump system between the one way valve and the intraprocedural device.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

BRIEF DESCRIPTION OF THE DRAWINGS

FIGS. 3A-3D are a top view, front view, perspective view and side view, respectively of an exemplary cap.

FIGS. 6A-6D are a cross-sectional view, side view, perspective view and a front view, respectively of an exemplary one-way valve.

FIG. 10 is a perspective view of yet another irrigation biopsy valve.

DETAILED DESCRIPTION

Figure 1:
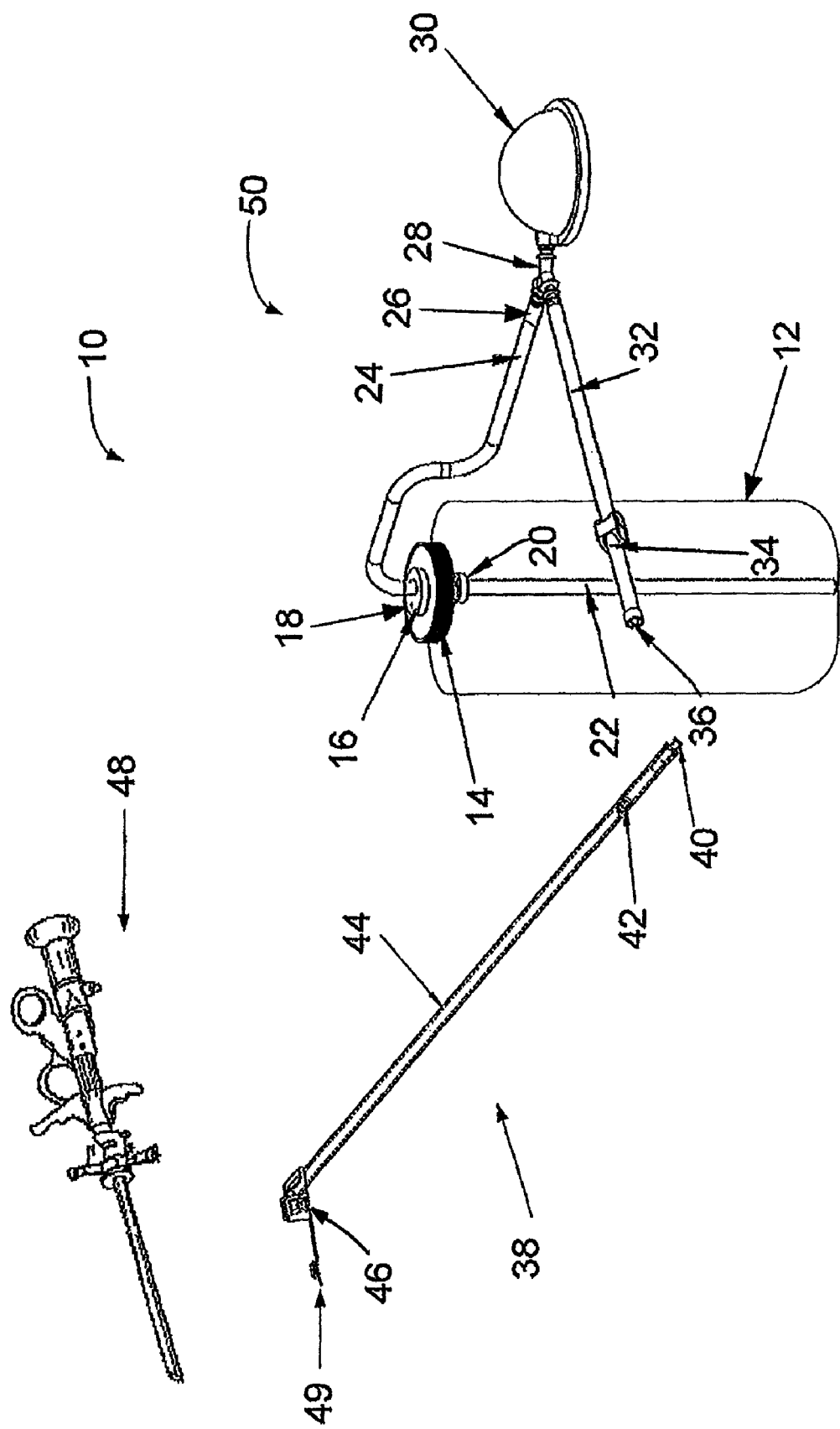
FIG. 1 is an environmental view of an exemplary intraprocedural irrigation system in accordance with the invention.

A physician performing a procedure often requires more irrigation fluid to clean off a procedural area then the irrigation channel of the endoscope can deliver. 60 cc syringes can be used to provide more irrigation fluid, but the use of 60 cc syringes is time consuming, awkward and leads to procedural delays. Syringes can leak at the biopsy valve thereby occupying the time of both the physician and assistants. This takes the physicians full attention away from the procedure. The use of the electrical pump devices can eliminate some of the problems associated with the 60 cc syringes, but the devices are unnecessarily complicated, and still do not provide sufficient volume, pressure and speed through the accessory channel of the endoscope to sufficiently clean tissue for a full inspection/viewing. These devices are costly (especially to have in every procedure room at a hospital or an outpatient office) and become even more costly when maintenance and repair of the devices are taken into account. Additionally, when the devices are receiving maintenance and repair, the physician is left without access to continual irrigation, leaving the physician with the same problems that the expensive machine was purchased to prevent.

A further problem resulting from the use of these alternative fluid supply devices is that the devices need to be reprocessed. According to the Society of Gastroenterology Nurses and Associates, water supplies, connectors and tubing should be manually cleaned and disinfected or sterilized on a daily basis. Therefore, the caps, tubing or other parts of the 60 cc syringes or pump systems need to be reprocessed before being used again. This reprocessing can be both costly and time consuming, can lead to delays between procedures, and does not offer each patient a new sterile product that has never been reprocessed.

As an alternative to the syringes and electrical pumps, certain pump systems that provide fluid from an I.V. bag are known in the art. U.S. Patent Application Publication 2005/0025646 to Miller et al. discloses a medical irrigation system. Fluid flows from I.V. bags down into an inlet valve of a pump thereby filling the pump with fluid. When the pump is actuated, the fluid flows out the outlet valve, and to a device such as an endoscope. This device relies solely on gravity to provide the fluid from the I.V. bags and is a less than optimal solution because the system must be disposed of or reprocessed/resterilized after each use.

U.S. Pat. No. 5,505,707 to Manzie et al. discloses a hand pump irrigation system. A continual low flow stream of fluid flows from I.V. bags, down through a pump and into a medical instrument. When a physician requires more fluid, a bolus of fluid can be delivered from the pump. This device also relies on gravity to provide the fluid from the I.V. bags and suffers from the whole system needing disposed of or reprocessed after one use. Additionally, this system actually prevents a continual high flow stream of fluid from entering the medical instrument because after the bolus of fluid is delivered from the pre-filled pump, and while the pump is refilling, fluid is still flowing to the medical instrument at the initial low flow rate. This continual low flow stream of fluid slows the refill of the pump and prevents a continual high flow stream from being delivered to the medical instrument. Even if the system could provide a continual high flow stream of fluid, the system occupies one of the physician's hands during use, making it impossible for the physician to operate the system while performing the procedure.

The disclosed technology recognizes the shortcomings with conventional irrigation systems, and provides a solution that allows a physician to provide a fluid to an intraprocedural device, such as an endoscope, ureteroscope, hysteroscope, etc., throughout an entire day's worth of procedures. This is accomplished while also allowing the physician to control the flow rate of the fluid. The manual irrigation pump is designed to give the physician optimum control of the flow rate and volume of irrigation fluid during the procedure. The system provides an immediate response when the physician engages the device by stepping on the pump and disengages the device by removing his/her foot. The manual foot pump thereby allows an assistant to attend to the needs of the patient and other requests from the physician without having to worry about supplying irrigation.

The principles of the invention will now be described with reference to the drawings. Referring to FIG. 1, an environmental view of an exemplary manual irrigation system 10 in accordance with the invention is shown. Manual irrigation system 10 operably couples to a medical instrument or intraprocedural device 48 to dispense irrigation fluids therefrom, and comprises a manual irrigation pump system 50 operably connected to a biopsy valve 38. The system 10 couples or otherwise connects to a water bottle 12 or other fluid reservoir that contains a fluid. A liquid supply tube 24 is coupled to a cap 14, or formed integrally with the cap 14, and placed in fluidic communication with the fluid in the water bottle 12 via another liquid supply tube 22. The other end of the liquid supply tube 24 is coupled to a connector 28. The connector 28 is also coupled to a manual foot pump 30 and a liquid supply tube 32. The liquid supply tube 24 delivers the fluid from the water bottle 12 to the manual foot pump 30 when the pump 30 is actuated, and the pump 30, in turn, delivers the fluid to the liquid supply tube 32. The liquid supply tube 32 is also coupled to biopsy valve 38, via fittings 36 and 40 (or the like), and the biopsy valve 38 is coupled to an intraprocedural device 48 by valve fitting 46. The fluid flows through the liquid supply tube 32, through the biopsy valve 38 and to the intraprocedural device 48 for irrigating the procedure site. The fluid source may be elevated to decrease fill time of the pump 30, however it will be appreciated that elevation of the fluid source is not required.

In this manner, the physician is able to provide a fluid to a procedure site while being able to control the flow rate and volume of the fluid. When the physician is finished with the procedure, the biopsy valve 38 can be disposed of and a new biopsy valve can be inserted in its place. Then, another procedure can be performed using manual irrigation pump system 50, described in more detail below, and the new biopsy valve 38. By following this procedure, the manual irrigation pump system 50 may be reused for multiple procedures while advantageously providing a new sterile biopsy valve 38 for every patient.

Figure 2:
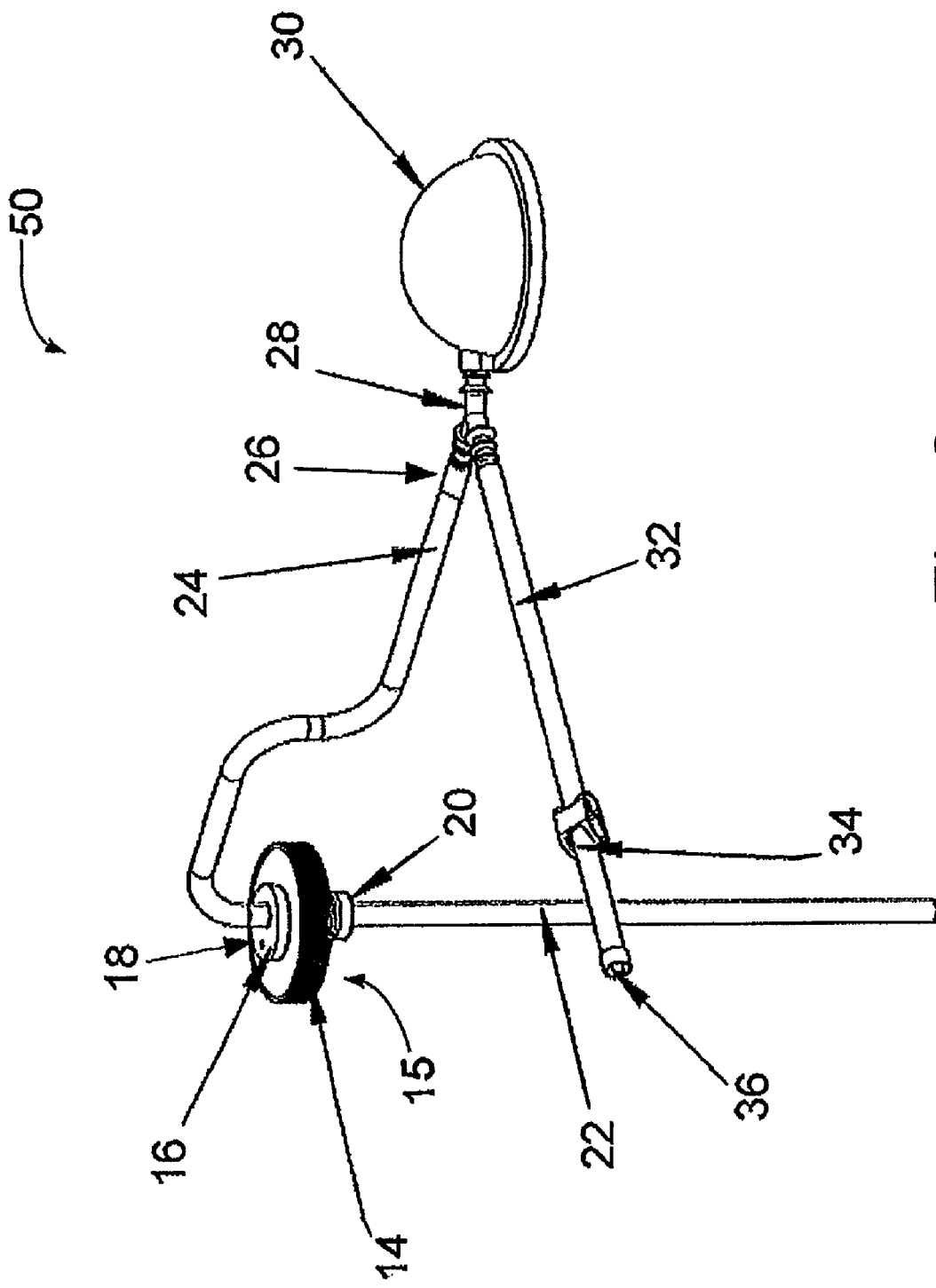
FIG. 2 is a perspective view of an exemplary manual irrigation pump system in accordance with the invention.

Referring now to FIGS. 1 and 2, the manual irrigation pump system 50 is described. The manual irrigation pump system 50 couples to a fluid source, represented as water bottle 12, which contains a fluid. Although described using the water bottle 12 as the fluid container, the fluid source may be any number of fluid sources such as an I.V. bag, a reservoir, etc. The water bottle 12 can be a reusable water bottle or a disposable water bottle, and the opening of the water bottle can be of varying diameters. To accommodate water bottles 12 with varying opening diameters, the system 50 includes the cap 14 having threads configured to couple to a water bottle 12 with a first opening diameter, and a stopper 16, or second cap having threads, disposed in the cap 14 configured to couple to a water bottle 12 of varying opening diameters that are less than the first diameter. For example, the cap may be designed to fit a water bottle with an opening of 2.5 inches.

During the procedure, when the cap 14 is coupled to the water bottle, if the water bottle has an opening diameter of 2.5 inches, then the cap 14 is threaded onto the bottle and the procedure can begin. If during the procedure the liquid in the water bottle 12 runs out, and the new water bottle has an opening diameter less than 2.5 inches (or the water bottle initially used has an opening diameter less than 2.5 inches), then the stopper 16 is coupled to the opening of the new water bottle and the procedure may continue. When the stopper 16 and the cap 14 are coupled to the water bottle 12, a sealed connection between the water bottle 12 and the system 50 is created, preventing fluid from leaking. In a preferred embodiment, a polypropylene cap having a liner, manufactured by United States Plastic Corp., may be used as cap 14.

The cap 14 also includes an air vent 18 configured to allow air to flow from the atmosphere to the water bottle 12. In at least one embodiment described below, the vent 18 can counteract pressure increases or decreases that occur in the water bottle when the pump system 50 is being used. Additionally, an antimicrobial filter (not shown) can be disposed in the cap 14 or water bottle 12 to ensure that there is no bacterial contamination in the water bottle 12, resulting from the introduction of ambient air into the bottle. And, if desired, an optional seal 15 (not shown) can be provided to seal between the cap 14 and the bottle 12. FIGS. 3A-3D provide further illustrations and some details of cap 14 described above, including the threaded portion of the cap, represented by reference numeral 58 and a through opening 17 may be provided to allow access to the fluids within bottle 12. The figures show a top view, front view, perspective view and side view, respectively of cap 14. The cross-section A-A, which is labeled in FIG. 3A, is shown in FIG. 3D.

Coupled to the cap 14 is the liquid supply tube 22, which places the cap 14 in fluidic communication with the fluid. A one-way valve 20 can be provided, as shown in FIG. 2, and may be located at the top of the liquid supply tube 22, in-between the cap 14 and the supply tube 22. The one-way valve 20 is used to limit the direction of fluid flow and can include a check-valve, a poppet valve, etc. The one-way valve 20 is oriented so that it restricts fluid flow so that the fluid flow is in the direction from the water bottle 12 toward the liquid supply tube 24 and not from the liquid supply tube 24 back toward the water bottle 12. In another embodiment, the valve 20 may be located at the bottom of the supply tube 22, which may help anchor the tube to the bottom of the water bottle 12, thereby minimizing the water left in the water bottle 12. In still another embodiment, the one-way valve 20 can be located between the cap 14 and liquid supply tube 24 (or disposed in the cap or liquid supply tube 24), used to couple the liquid supply tube 24 with the cap 14.

With continued reference to FIG. 2, the supply tube 24 can have a proximal end that is coupled to the cap 14 and a distal end that is coupled to one of the openings in connector 28. The supply tube 24 may be coupled to the cap 14 by a fitting, a one-way valve described in FIG. 6, etc. or may have a fitting integrated into its design. Alternatively, the liquid supply tube 24 may run through the cap and replace liquid supply tube 22 or be integrally formed with the cap 14, and therefore not require a fitting to couple with the cap 14.

Disposed in or otherwise operatively coupled to the liquid supply tube 24 is an optional one-way valve 26, oriented so that it restricts fluid flow so the fluid flow is in the direction from the pump 30 toward the liquid supply tube 32 and not from the pump 30 back toward the liquid supply tube 24. This prevents fluid expelled from the pump 30 from flowing back to the first liquid supply tube 24 thereby hindering the fluid flow to the biopsy valve 38. The one-way valve 26 may include a check-valve, a poppet valve, etc., and, in addition to being disposed in the liquid supply tube 24, the valve 26 may also be disposed in a first opening of connector 28 that couples the connector 28 to liquid supply tube 24. As mentioned above, one-way valve 26 is an optional valve. One-way valve 20, which may be configured in any location between the supply tube 22 and the pump 30, may be used to as the only valve to prevent fluid flow from the pump 30 to the water bottle 12.

Coupled to a second opening of the connector 28 is the liquid supply tube 32. The liquid supply tube 32 has a proximal end coupled to the connector 28, and a distal end operatively coupled to or having an integrated fitting 36. The fitting 36 is used to releasably couple the liquid supply tube 32 to the removable and replaceable biopsy valve 38 via fitting 40 on the biopsy valve 38. In this example, the fitting 36 on liquid supply tube 32 is a luer lock-type fitting, but the fitting 36 may be any type of fitting such as a hose barb, a hose coupler, etc. Optionally included on liquid supply tube 32 is a pinch clamp 34, which can be used to stop the fluid flow into the biopsy valve 38 at any time. Also optionally included in the liquid supply tube 32 is another optional one-way valve (not shown). The optional one-way valve can be used in place of the pinch clamp 34, although the valve and clamp 34 can be used in conjunction with one another. The optional one-way valve can be used to prevent the fluid from flowing into the biopsy valve 38 and towards the intraprocedural device 48 below a certain system pressure. For example, if the pressure needed to open the optional one-way valve is normally 3 psi above atmospheric pressure when the pump is actuated, then a 3 psi check valve may be used for the optional one-way valve to prevent fluid flow at less than 3 psi when a pressure of less than 3 psi is applied to the pump. When the physician or operator needs to immediately stop fluid flow, he/she removes his/her foot from the pump 30, but some fluid will already be in liquid supply tube 32 flowing toward the intraprocedural device 48. Because the physician is no longer actuating the pump 30, the fluid in the tube will be flowing at less than 3 psi, and therefore because of the 3 psi check valve the fluid will not enter the intraprocedural device 48. The 3 psi check valve can also allow a system pressure below about 3 psi to be maintained within the portions of the manual irrigation pump system 50 proximal to or upstream to the 3 psi check valve. In some embodiments, air vent 18 can be used to bleed down the system pressure caused by the 3 psi check valve.

Referring now to the connector 28 in more detail, the connector 28 as shown is a y-connector used to bifurcate the flow of fluid in and out of pump 30. The connector can be made from any suitable material. Although a y-connector is shown, other types of connections may be used as long as the connection bifurcates the fluid flow. A first opening of the connector 28 is coupled to liquid supply tube 24, a second opening is coupled to liquid supply tube 32 and a third opening is coupled to the pump 30. Using the connector 28, the pump 30 is only required to have one opening 54, thereby simplifying construction and decreasing chances of leaking or other problems associated with fluid pumps having multiple openings. Further, by using connector 28 with pump 30, the liquid supply tubes 24 and 32 can be located to prevent the physician from getting tangled in the tubes 24 and 32 or from accidentally stepping on the tubes 24 and 32 and interrupting fluid flow.

Figure 4A:
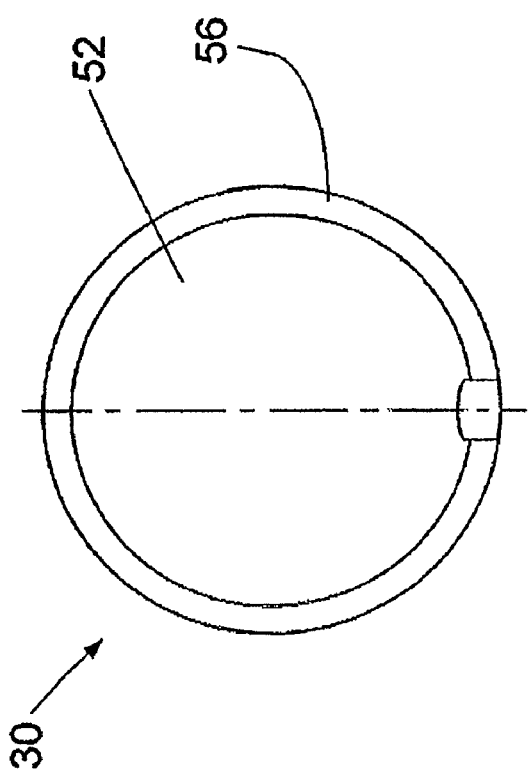
FIGS. 4A-4C are a top view, front view and side view, respectively of an exemplary manual foot pump.
Figure 4C:
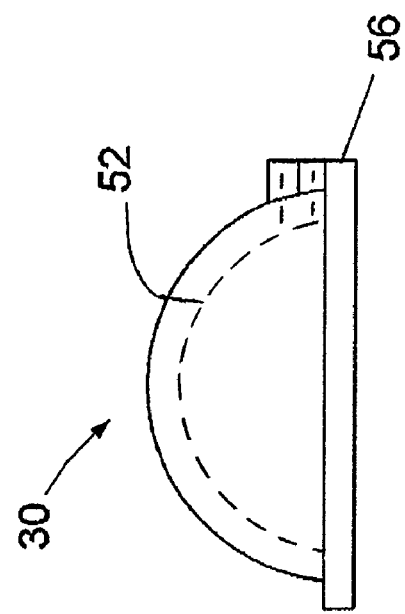
Figure 4B:
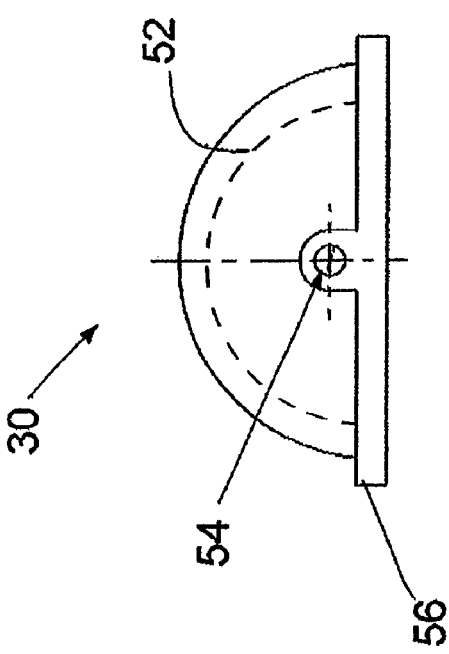

Referring now to manual foot pump 30 in more detail, FIGS. 4A-4C provide a top view, front view and side view, respectively of the manual foot pump 30 which can include one or more hollows or chambers (see dashed lines in FIG. 4) within operably coupled to opening 54. The chamber of the pump 30 is represented by reference numeral 52 and can occupy a substantial portion of the interior of the pump 30. When the pump 30 is actuated such as by compressing the pump 30 to decrease the volume of the chamber 52, the pump body physically deflects or elastically deforms and fluid is delivered from the pump 30 to the intraprocedural device 48 via opening 54. Pump 30 can be constructed from an elastomeric or resilient material that can be deformed under a force such as but not limited to foot pressure, yet generally return to an un-deformed shape shown in FIGS. 4A-4C upon removal of the force or pressure. The material properties of the pump 30 can be further configured to provide sufficient force to draw fluid into the chamber 30 as the pump 30 moves from the deformed shape to the un-deformed shape.

The actuation of the pump 30 requires an operator (such as a surgeon) to physically deliver mechanical work to the pump 30 to pressurize the manual irrigation pump system 50. Mechanical work requires the surgeon or operator to apply a physical force over a distance and it is the mechanical work or energy delivered by the physical action of the operator over the distance that provides the energy to pressurize system 50 and to propel fluid into the intraprocedural device 48.

For example, but not limited thereto, the physical force can be a pressure applied to the pump 30 with a foot, a hand, or an elbow to create the motive pressure on fluid contained therein. With pump 30, the force input is directly proportional to the pump pressure and fluid flow from the pump 30. That is, more force on the pump 30 equates to higher pump pressures and more flow, and less force on the pump 30 equates to lower pump pressures and less flow. Thus, any input of arcuate or linear force physically applied over distance by any portion of an operator's anatomy is a manual transfer of mechanical work from the operator to the pump 30 to propel an amount of fluid from the manual irrigation pump system 50. Since the operator provides the mechanical work, the operator can easily control of the flow rate and volume of irrigation fluid during a procedure. Should the operator deplete or empty the fluid from the chamber 52 from a sustained application of pressure, the chamber 52 can be refilled by simply removing the operator's contact from the pump 30 and allowing the pump 30 to return to the un-deformed shape.

As is discussed above, one-way valve 20 and optional one-way valve 26 limit the direction in which the fluid can flow. The pump 30 includes a base 56 or other support, which allows the pump 30 to sit flat against the floor or other surface to prevent the pump 30 from changing positions during the procedure. When the physician removes his or her foot, thereby releasing the pump 30, the fluid is drawn from the water bottle 12 into chamber 52 via opening 54. The volume and flow rate of fluid is dictated by the pressure and duration of pulses provided by the physician.

The quick refill time, along with other features of the system 50, allows the physician to control the pressure, volume, and flow rate of the water. Before each procedure, the pump 30 can be primed to remove air from the system 50 and allow the physician to have immediate access to irrigation. In a preferred embodiment, a pump such as one manufactured by Albert International may be used. Although the pump 30 is described as a foot pump, other types of manual pumps may be used such as hand operated pumps, spring operated foot pedals, etc. Additionally, although the pump 30 is described having only one opening, a pump with a first opening for the first liquid supply tube 24 and a second opening for the second liquid supply tube 32 may be used. In the dual opening pump example, a connector is not required to place the parts in fluidic communication, although one may be used.

Figure 5:
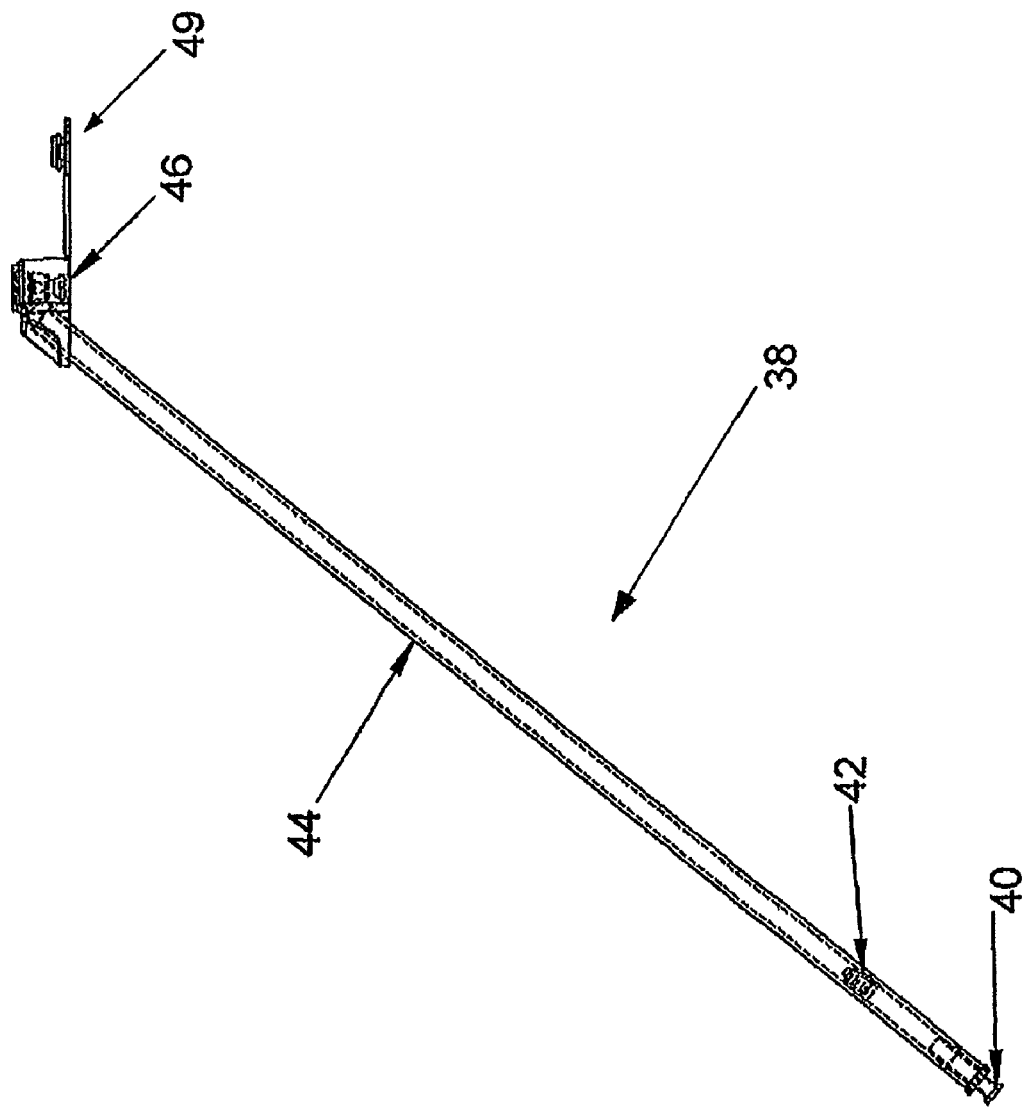
FIG. 5 is a perspective view of an exemplary irrigation biopsy valve.

Referring now to FIG. 5, a perspective view of exemplary irrigation biopsy valve 38 is shown. The biopsy valve 38 includes a fitting 40, a one-way valve 42, a liquid supply tube 44, and a valve fitting 46. The liquid supply tube 44 of biopsy valve 38 has a proximal end that is integrally coupled to the fitting 40, and a distal end that is integrally coupled to the valve fitting 46. The irrigation valve 46 removably couples to an accessory water channel of the intraprocedural device 48, allowing the biopsy valve 38 to be easily attached and detached from the accessory channel of the intraprocedural device 48 and preventing leakage around the accessory channel. If desired, the biopsy valve 38 may have an opening for insertion of other devices into the accessory channel. Valve fitting 46 can be constructed from a flexible or elastomeric material such as but not limited to rubber, urethane, or silicone. In one embodiment, a valve cap 49 is provided. The valve cap 49 can be configured to lock with the valve fitting 46, and can be used to seal the top portion of the valve fitting 46. In some embodiments, valve cap 49 can be integrally attached to the valve fitting 46 or an integral portion thereof. Valve fitting 46 can be constructed from a flexible or elastomeric material described above, or configured as an integral part of valve fitting 46, and the integrally attached valve cap 49 can be flexibly deflected into locking engagement with valve fitting 46.

In an alternate embodiment, the valve cap 49 can be secured to the top portion of the valve fitting 46 by an alternate securing system comprising one or more securing members 90 (not shown). The one or more securing members 90 are configured to engage with one or more features on valve fitting 46 and/or the intraprocedural device 48 to hold the valve cap 49 in sealing engagement with the valve fitting 46. The one or more features on valve fitting 46 can be as shown, or can be or a member or feature added to an exterior of the valve fitting 46 such as a rib, a snap, a detent, and the like. In another embodiment, but not limited thereto, the securing members 90 can be an integral portion of the valve fitting 46 and can be flexibly deflected to securely engage with features on valve fitting 46 and/or the intraprocedural device 48 to hold the valve cap 49 in sealing engagement with valve fitting 46. The fitting 40 is used to removably couple the biopsy valve 38 to the fitting 36 of the liquid supply tube 32. In this example, the fitting 40 is a luer lock-type fitting. If the fitting 36 is a male luer lock-type fitting then the fitting 40 can be a female luer lock-type fitting or the reverse. Other fittings may be used, however, such as hose barbs, hose couplers, etc. Above the fitting 40, or alternatively disposed in the fitting 40, is a one-way valve 42. The one-way valve 42 is oriented so that it restricts fluid flow so the fluid flow is in the direction from the fitting 40 toward the liquid supply tube 44 and not from the liquid supply tube 44 back toward liquid supply tube 32. The one-way valve 42 prevents fluid in the biopsy valve 38 from flowing back toward liquid supply tube 32 and confines the backflow fluids to the portion of the biopsy valve 38 located between the valve fitting 46 and the one-way valve 42. This allows the pump system 50 to be used for multiple procedures while only having to dispose the biopsy valve 38 to provide each new patient with sterile parts and sterile fluids, and without reprocessed components.

Referring to FIGS. 6A-6D, a cross-sectional view, side view, perspective view and a front view, respectively of an exemplary one-way valve 60 is shown. FIG. 6A shows a partial cross-sectional view of the valve 60, taken from section B-B, which along with direction of the flow, is labeled in FIG. 6B. The one-way valve 60 may be used as valves 20, 26, or 42 described above, although other valves may be used, such as valves being disposed in the liquid supply tubes or connectors. Valve 60 has a first end 62 and a second end 64 configured and sized for insertion into the liquid supply tubes and other parts. For example, using valve 60 as one-way valve 20, the first end 62 of the valve 60 can be inserted into the stopper 16/cap 14, and the second end 64 of the valve 60 can be inserted into the liquid supply tube 24. The valve places the two parts in fluidic communication with one another and prevents fluid from flowing back into the water bottle 12. One-way valves are well known in the art, can include springs or other pressure control devices, and in a preferred embodiment, a precision molded check valve with a silicone diaphragm, manufactured by Ark-Plas Products, Inc., may be used.

Figure 7:
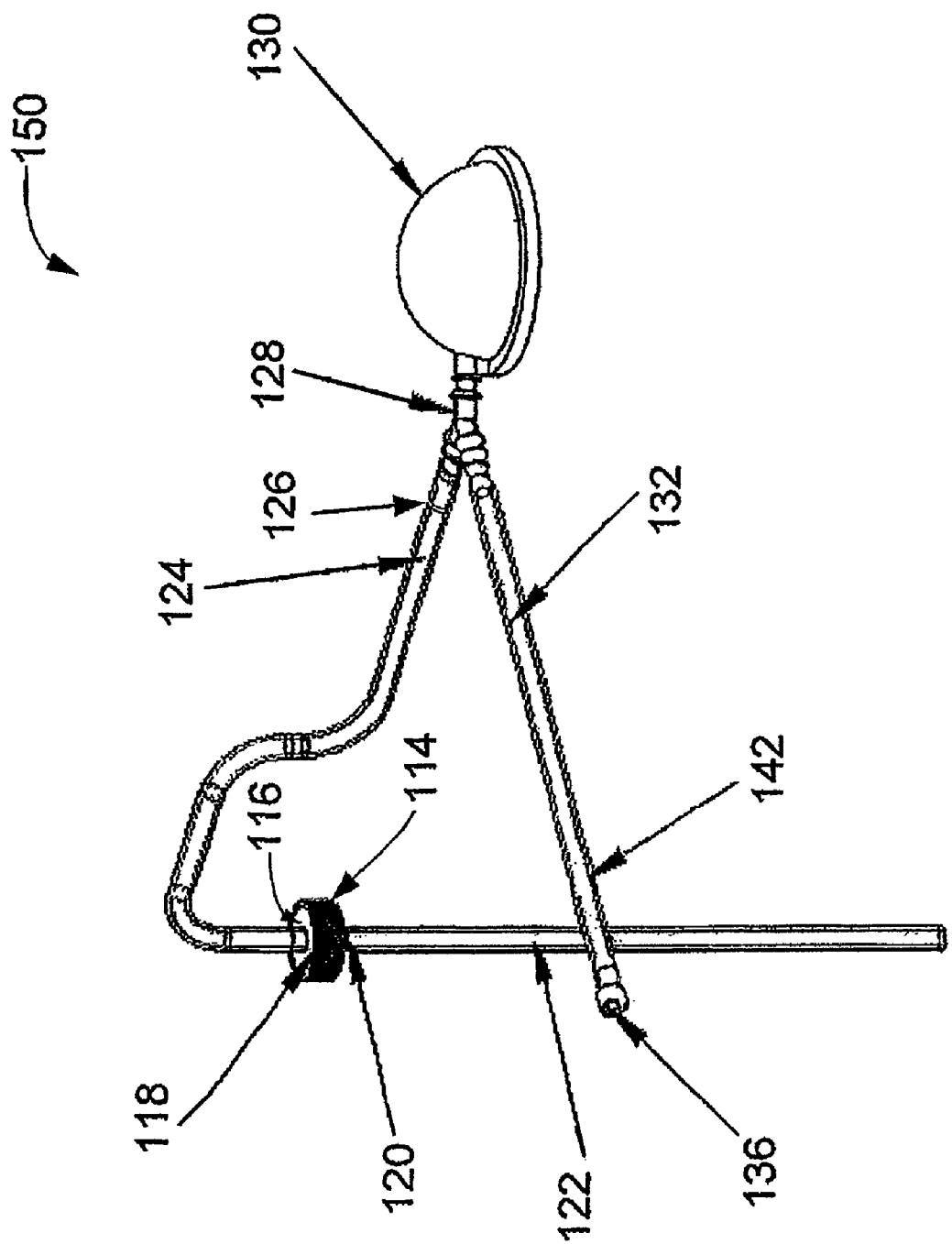
FIG. 7 is a perspective view of another manual irrigation pump system in accordance with the invention.
Figure 8:
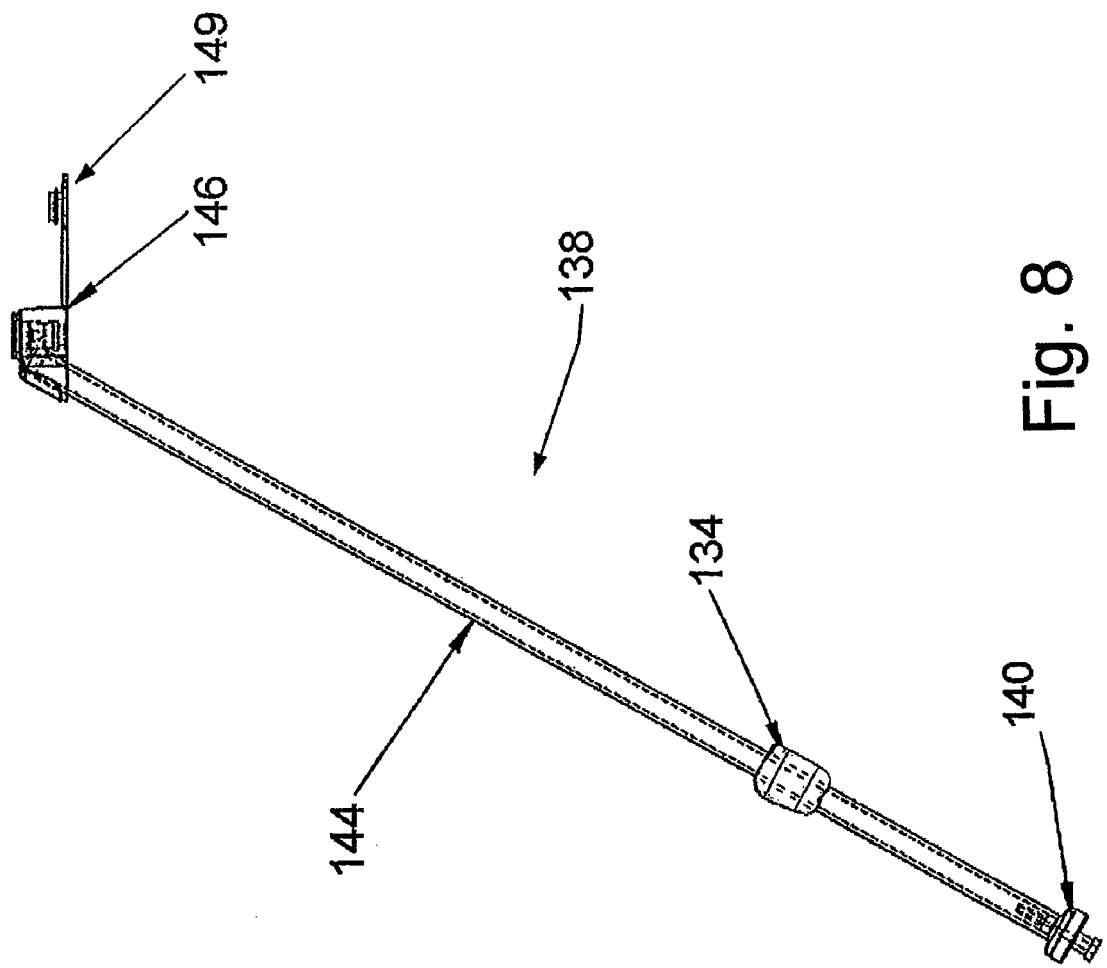
FIG. 8 is a perspective view of another irrigation biopsy valve.

Turning now to FIGS. 7 and 8, another embodiment of manual irrigation pump system and irrigation biopsy valve is indicated generally by reference numerals 150 and 138, respectively. The pump system 150 and biopsy valve 138 are substantially the same as the above-described pump system 50 and biopsy valve 38, and consequently the same reference numerals, but indexed by 100 are used to denote structures corresponding to similar structures in the pump system 50 and biopsy valve 38. In addition, the foregoing description is equally applicable to the pump system 150 and biopsy valve 138 except as noted below. The pump systems 50 and 150 and biopsy valves 38 and 138 can be used in any combination based on the desired application.

Figure 9:
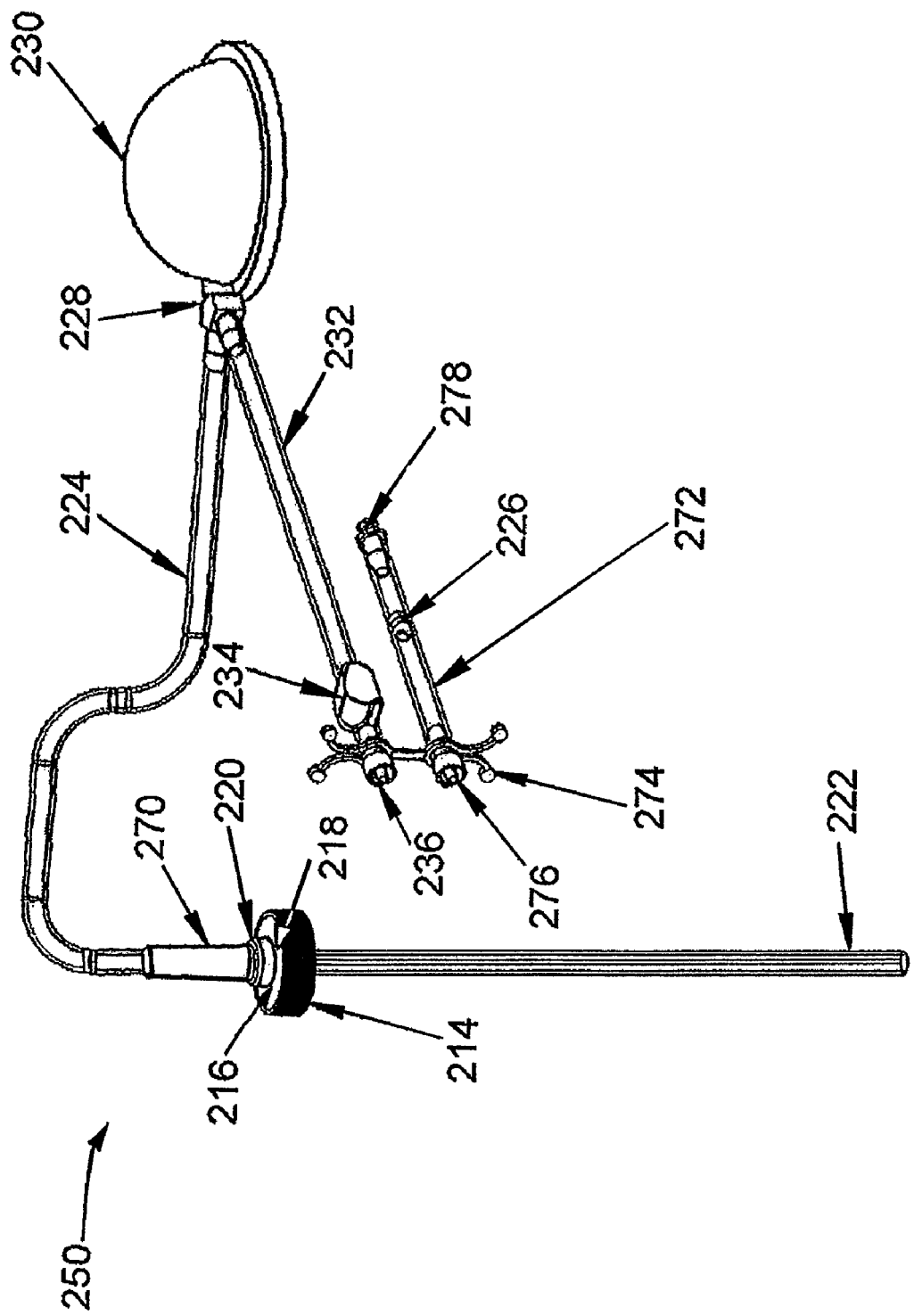
FIG. 9 is a perspective view of yet another manual irrigation pump system in accordance with the invention.

Referring to FIG. 7, the manual irrigation pump system 150 is shown. The pump system 150 includes an optional one-way valve 126, disposed in or otherwise operatively coupled to the liquid supply tube 124, and oriented so that it restricts fluid flow so the fluid flow is in the direction from the pump 130 toward the liquid supply tube 132 and not from the pump 130 back toward the liquid supply tube 124. The pump system 150 also includes another one-way valve 142 that replaces or can be used in conjunction with the pinch clamp shown in FIG. 2. The one-way valve 142 is disposed in or otherwise operatively coupled to the liquid supply tube 132 and is oriented so that it restricts fluid flow so the fluid flow is in the direction from the liquid supply tube 132 toward the biopsy valve 138 and not from the biopsy valve 138 back toward the pump 130. A fitting 136 is also located at a distal end of the liquid supply tube 132 and configured to operably and removably engage with the biopsy valve 138. Referring now to FIG. 8, the irrigation biopsy valve 138 is shown. Included on the biopsy valve 138 is a pinch clamp 134 that replaces or can be used in conjunction with the one-way valve shown in FIG. 5. The pinch clamp 134 can be used by the operator to stop the fluid flow through the liquid supply tube 144 at any time, and can be opened to resume fluid flow at any time. A one-way valve 140 can also be provided with the liquid supply tube 144, and is shown adjacent to a proximal end of the tube 144 to prevent backflow into the liquid supply tube 132. A valve cap 149 and valve fitting 146 can be attached to a distal end of the liquid supply tube 144, and can perform the same functions as the previously described valve cap 49 and valve fitting 46, respectively. Turning now to FIGS. 9 and 10, another embodiment of manual irrigation pump system and irrigation biopsy valve is indicated generally by reference numerals 250 and 238, respectively. The pump system 250 and biopsy valve 238 are substantially the same as the above-described pump system 50 and biopsy valve 38, and consequently the same reference numerals, but indexed by 200 are used to denote structures corresponding to similar structures in the pump system 50 and biopsy valve 38. In addition, the foregoing description is equally applicable to the pump system 250 and biopsy valve 238 except as noted below. The pump systems 50, 150 and 250 and biopsy valves 38, 138 and 238 can be used together in any combination based on the desired application.

Referring now to FIG. 9, the manual irrigation pump system 250 is shown. The pump system 250 includes a one-way valve 220, which is located above the cap 214, in-between the cap 214 and connector 270. The one-way valve 220 is oriented so that it restricts fluid flow so that the fluid flow is in the direction from the water bottle 212 toward the liquid supply tube 224 and not from the liquid supply tube 224 back toward the water bottle 212. In another embodiment, the valve 220 may be located at the bottom of the supply tube 222, which may help anchor the tube to the bottom of the water bottle 212, thereby minimizing the water left in the water bottle 212. In still another embodiment, the one-way valve 220 can be located at the top of the liquid supply tube 222, in-between the cap 214 and the supply tube 222 (or disposed in the cap or liquid supply tube 224).

With continued reference to FIG. 9, the supply tube 224 has a proximal end that is coupled to the connector 270 and a distal end that is coupled to one of the openings in connector 228. The supply tube 224 may be coupled to the connector 270 by a fitting, be integrated with the connector 270, etc., or may have a fitting integrated into its design. The connector 270, which can have one end coupled to the supply tube 224 and another end coupled to the one-way valve 220, is provided to prevent the supply tube 224 from bending, kinking, etc. during use, thereby insuring that the fluid can flow through the supply tube 224.

Coupled to a second opening of the connector 228 is the liquid supply tube 232. The liquid supply tube 232 has a proximal end coupled to the connector 228, and a distal end coupled to or having an integrated fitting 236. The fitting 236 is used to couple the liquid supply tube 232 to the biopsy valve 238 via fitting 240 or to couple a liquid supply tube 272 to the liquid supply tube 232 via fitting 278. In this example, the fittings are luer lock-type fittings, but the fittings may be any type of fitting such as a hose barb, a hose coupler, etc. Included on liquid supply tube 232 is a pinch clamp 234, which can be used to start or stop the fluid flow into the biopsy valve 238 at any time.

Also included in the pump system 250 is a coupler 274. The coupler 274 may be configured to releasably retain supply tube 272 to and supply tube 232 together, thereby allowing easy access to supply tube 272. If desired by the operator, the supply tube 272 may be coupled to the supply tube 232 and the biopsy valve 238 via fittings 278 and 276, respectively. The supply tube 272 can have a one-way valve 226 disposed in or coupled to supply tube 272, which can be used to prevent the fluid from flowing into the biopsy valve 238 below a certain pressure.

Referring now to FIG. 10, a perspective view of irrigation biopsy valve 238 is shown. The biopsy valve 238 includes a fitting 240, a one-way valve 242, liquid supply tubes 244 and 280, a valve fitting 246, and a pinch clamp 282. The liquid supply tube 280 has a proximal end that is coupled to the fitting 240, and a distal end that is coupled to the one-way valve 242. The liquid supply tube 244 has a proximal end that is coupled to the one-way valve 242 and a distal end that is coupled to the valve fitting 246 which is shown with a valve cap 249 removably sealing an opening in valve fitting 246. It will be appreciated that the one-way valve 242 may be disposed in one of the supply tubes 244 or 280 or that the biopsy valve 238 may include only one supply tube. The one-way valve 242 is oriented so that it restricts fluid flow so the fluid flow is in the direction from the liquid supply tube 280 toward the liquid supply tube 244 and not from the liquid supply tube 244 back toward liquid supply tube 232.

Included on one of the supply tubes 244 or 280 is pinch clamp 282, which can be used by the operator to stop or start the fluid flow through the liquid supply tube 244 or 280 at any time. Included at one end of the biopsy valve 238 is the irrigation valve fitting 246 configured to couple to an accessory water channel of the intraprocedural device (not shown), allowing the biopsy valve 238 to be easily attached and detached from the accessory channel of the intraprocedural device (not shown) and preventing leakage around the accessory channel. If desired, the biopsy valve 38 may have an opening for insertion of other devices into the accessory channel. In one embodiment, a valve cap 49 is provided. The valve cap 49 can be used to seal the top portion of the valve fitting 46 and could also have device access.

At the other end of the biopsy valve 238 is the fitting 240, configured to couple the biopsy valve 238 to the fitting 236 or 276 of the liquid supply tube 232. In this example, the fitting 240 is a luer lock-type fitting. If the fitting 236 or 276 is a male luer lock-type fitting, then the fitting 240 can be a female luer lock-type fitting or the reverse. Other fittings may be used, however, such as hose barbs, hose couplers, etc.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A disposable manual irrigation pump system comprising:
   a manual foot pump configured to be coupled to a fluid reservoir and an intraprocedural device, the foot pump being configured to draw fluid from the fluid reservoir into the foot pump to substantially fill the foot pump as the foot pump moves from a deformed state to an un-deformed state;
   a first one-way valve disposed between the foot pump and the reservoir;
   a first liquid supply tube disposed between the pump and the reservoir and a second liquid supply tube disposed between the pump and the intraprocedural device;
   a connector configured to couple an end of the first liquid supply tube and an end of the second liquid supply tube to the pump;
   wherein the pump system is configured to provide a substantially continuous fluid supply at a desired flow rate from the fluid reservoir to the intraprocedural device along a first direction and the one-way valve is configured to prevent backflow of fluid along a direction opposite the first direction;
   wherein the connector is a Y-connector having one opening coupled to the first liquid supply tube, one opening coupled to the second liquid supply tube, and one opening coupled to the pump; and
   wherein the pump includes a single opening, the single opening being connected to the Y-connector.

2. A disposable manual irrigation pump system comprising:
   a manual foot pump configured to be coupled to a fluid reservoir and an intraprocedural device, the foot pump being configured to draw fluid from the fluid reservoir into the foot pump to substantially fill the foot pump as the foot pump moves from a deformed state to an un-deformed state; and
   a first one-way valve disposed between the foot pump and the reservoir;
   wherein the pump system is configured to provide a substantially continuous fluid supply at a desired flow rate from the fluid reservoir to the intraprocedural device along a first direction and the one-way valve is configured to prevent backflow of fluid along a direction opposite the first direction; and wherein the pump includes a single opening through which fluid is received in the pump from the reservoir and through which fluid is delivered from the pump to the intraprocedural device.

3. The disposable manual irrigation pump system of claim 2, further comprising a first liquid supply tube disposed between the pump and the reservoir and a second liquid supply tube disposed between the pump and the intraprocedural device.

4. The disposable manual irrigation pump system of claim 3, further comprising a connector configured to couple an end of the first liquid supply tube and an end of the second liquid supply tube to the pump.

5. The disposable manual irrigation pump system of claim 4, further comprising a second one-way valve disposed between the pump and the intraprocedural device, wherein the second one-way valve allows fluid to flow from the pump to the intraprocedural device without backflow of fluid from the intraprocedural device to the pump.

6. The disposable manual irrigation pump system of claim 5, wherein the first one-way valve allows fluid to flow from the reservoir to the pump without backflow of fluid from the pump to the reservoir.

7. The disposable manual irrigation pump system of claim 4, wherein the connector is a Y-connector having one opening coupled to the first liquid supply tube, one opening coupled to the second liquid supply tube, and one opening coupled to the pump.

8. The disposable manual irrigation pump system according to claim 3, further comprising an irrigation valve configured to couple the intraprocedural device and the second liquid supply tube.

9. The disposable manual irrigation pump system according to claim 2, further comprising a connector disposed between the pump and the reservoir, wherein the connector is configured to insure the fluid flow is unimpeded through first liquid supply tube.

10. The disposable manual irrigation pump system according to claim 8, further comprising a third liquid supply tube disposed between the second liquid supply tube and the irrigation valve, wherein the third liquid supply tube is configured to couple the second liquid supply tube and the irrigation valve.

11. The disposable manual irrigation pump system according to claim 10, further comprising a coupler, wherein the coupler is configured to retain the second and third liquid supply tubes.

12. The disposable manual irrigation pump system of claim 2, further comprising a cap having threads suitable for coupling to a fluid reservoir having a first diameter and a stopper or second cap having threads suitable for coupling to a fluid reservoir having a second diameter.

13. The disposable manual irrigation pump system of claim 12, wherein the cap further includes an air vent configured to allow air to flow into the fluid reservoir.

14. The disposable manual irrigation pump system of claim 12, further comprising a liquid supply tube disposed in an opening of the cap.

\* \* \* \* \*